United States Patent [19]

Hoyer et al.

[11] 4,354,838
[45] Oct. 19, 1982

[54] FOOT CONTROLLER FOR DENTAL INSTRUMENTS OR THE LIKE

[75] Inventors: Gerd Hoyer, Karlsruhe; Helmut Pietschmann, Karlsbad, both of Fed. Rep. of Germany

[73] Assignee: Sybron Corporation, Rochester, N.Y.

[21] Appl. No.: 240,598

[22] Filed: Mar. 4, 1981

[30] Foreign Application Priority Data

May 6, 1980 [DE] Fed. Rep. of Germany ....... 3017245

[51] Int. Cl.³ .............................................. A61C 1/02
[52] U.S. Cl. .................................................. 433/101
[58] Field of Search .................. 433/101; 200/153; 318/551, 153 C

[56] References Cited

U.S. PATENT DOCUMENTS

| 3,067,765 | 12/1962 | Aymar et al. | 433/101 |
| 4,041,609 | 8/1977 | Bresnahan | 433/101 |
| 4,118,866 | 10/1978 | Ross | 433/101 |

Primary Examiner—Robert Peshock
Attorney, Agent, or Firm—Theodore B. Roessel; Roger Aceto

[57] ABSTRACT

A foot controller for dental instruments having a pair of foot pedals which are depressed to initiate and control the rate of flow of a utility service, there being a single, variable output generator with the controller which can be operated by either the independent or simultaneous operation of the foot pedals.

10 Claims, 3 Drawing Figures

FOOT CONTROLLER FOR DENTAL INSTRUMENTS OR THE LIKE

BACKGROUND OF THE INVENTION

The present invention relates to a foot controller as may be used to control the operation of a variety of dental instruments such as drills, syringes, scalers or the like. In particular, the foot controller of the present invention functions to permit both selection and control of a utility source such as air, water or electricity simply by stepping on a single pedal which is hinged for movement about a horizontal axis.

Foot controllers are known that have a single horizontally swinging foot operated lever to control variables such as speed of an air or electrically driven handpiece. In some cases, the lever can be biased to a neutral position so the movement of the lever to either side of neutral will control a different function. In a foot controller as shown in U.S. Pat. No. 3,471,928, the control element is a ring which is pivoted about a vertical axis to either side of a neutral position. The farther the ring is moved from the neutral position, the greater the speed or flow. Separate foot operated switches are used to select the utility such as air, water or spray while movement of the ring controls the flow rate of the selected utility as needed.

In another known foot controller, as shown in German Pat. No. 2,530,108, a foot pedal is depressed for switching on the particular instrument to be controlled. The pedal is then tilted in one direction or another to raise or lower the speed of the instrument. By simultaneously stepping on a second pedal, a switch is operated which additionally makes possible the release of cooling water from the instrument.

In the present invention, simply stepping on a foot pedal and depressing it about a horizontal axis acts both to select the utility service desired and to control the rate of flow of the service. The foot control of the present invention has two such pedals both acting on a single regulator capable of providing a variable output depending upon the position of the foot pedal. Each pedal is in turn connected to a switch which is associated with the desired utility so that upon operation of the foot pedal both the initiation and the control of the flow of the selected utility is achieved.

SUMMARY OF THE PRESENT INVENTION

The present invention may be characterized in one aspect thereof by the provision of a pair of foot pedals, each hinged for movement about a horizontal axis; a signal generator capable of producing an output signal in response to the movement of a single control element; separate operating mechanisms between each pedal and the single control element for moving the control element responsive to either independent or simultaneous movement of the foot pedals; and a utility on/off switch associated with each operating mechanism for switching on an appropriate utility supply responsive to movement of the foot pedals.

DESCRIPTION OF THE PREFERRED EMBODIMENTS

Figure 1:
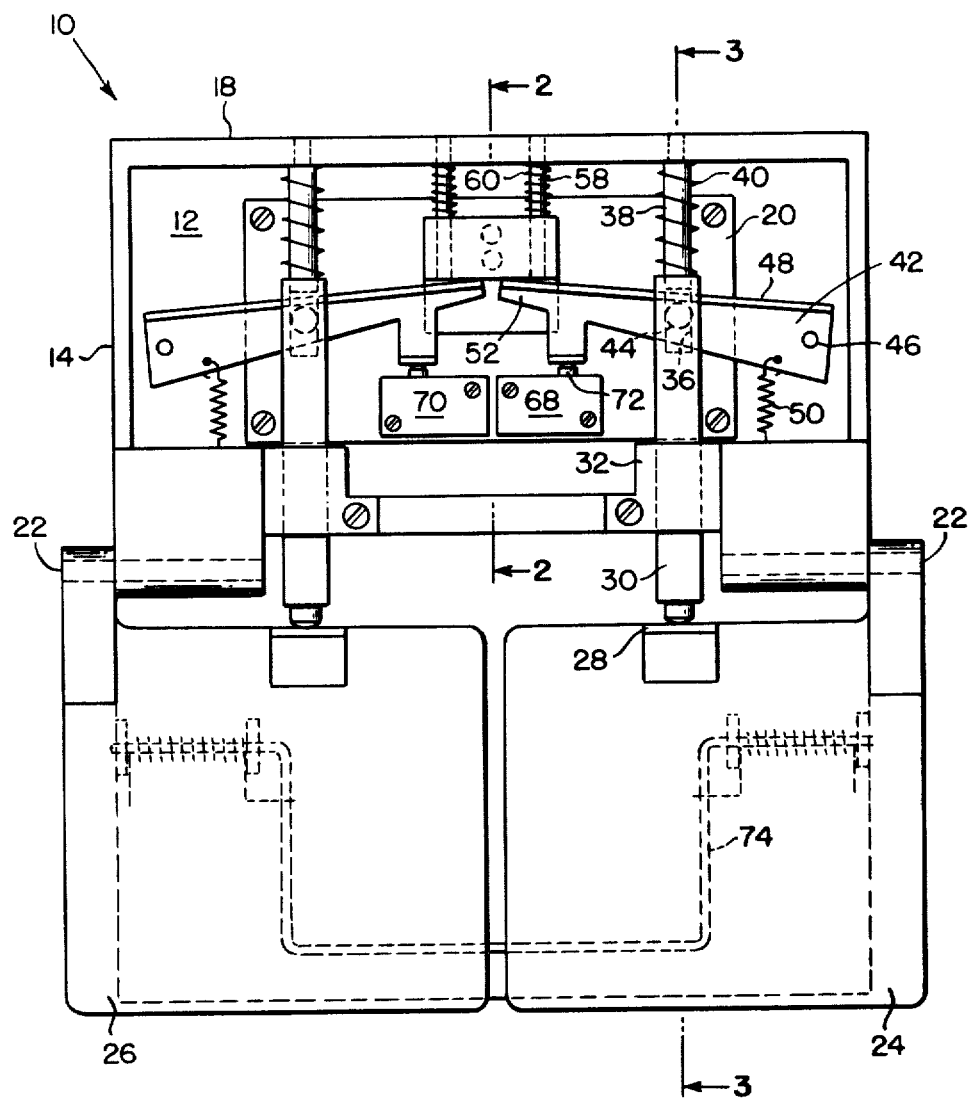
FIG. 1 is a top view of the foot controller with portions removed to show internal components.
Figure 3:
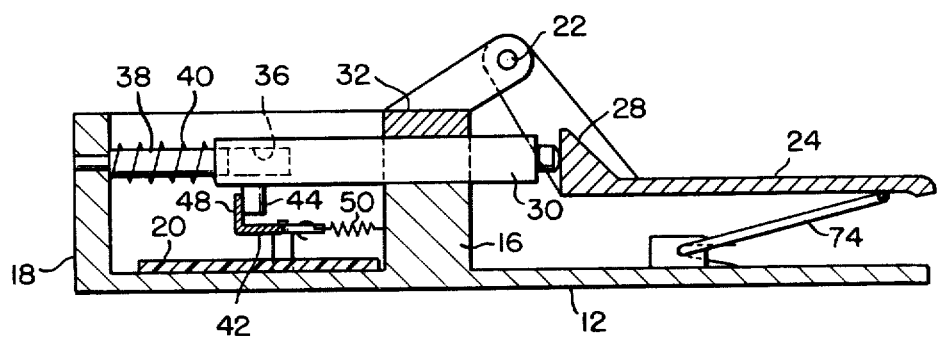
FIG. 3 is a view taken along lines 3—3 of FIG. 1.

Referring to the drawings, FIGS. 1 and 3 show the foot controller of the present invention generally indicated at 10 to include a base 12 adapted to rest on a floor surface. This base carries a housing 14 which has upstanding front and rear walls 16, 18 respectively. Within the housing is a printed circuit board 20 on which is mounted various components of the foot controller. It should be appreciated that while the housing contains various mechanical and electrical components of the controller as described hereinbelow, various parts of the controller as well as all electrical connections and lead wires have been removed for purposes of clarity. Also not shown are additional switching devices known in the art for accomplishing such functions as the reversal of direction of rotation of an electrically driven handpiece or for the operation chip blowers. In any event, the parts not shown are not required for an understanding of the invention as claimed.

Journaled to the upper end of front wall 16 for rotation about a horizontal axis 22 are two foot pedals 24 and 26. It should be appreciated that to a certain extent the components of the foot controller within housing 14 are duplicated for each foot pedal. Accordingly, only one set of such components as may be associated with foot pedal 24 will be described and it should be understood that except as specified, a similar set of components would be associated with, and independently operated by, foot pedal 26.

Each pedal 24, 26 has an upstanding member 28 which bears against one end face of a generally horizontal bar 30. Bar 30 extends slidably through a recess in the housing front wall 16. This recess and a cover plate 32 provide guide means for bar 30.

Extending axially inward from the opposite end face of bar 30 is a bore 36. This bore slidably receives a mandrel 38, which is threaded through the housing rear wall 18. A coil spring 40 biased between the mandrel and bar 30 urges the bar in a direction to the right as shown in FIG. 3. With the arrangement thus far described, stepping on foot pedal 24 will cause bar 30 to move to the left as viewed in FIG. 3 against the bias of spring 40.

Carried by and extending downwardly from bar 30 is a pin 44 (FIG. 3). This pin is adapted to engage against an upstanding portion 48 of a lever 42. Lever 42 is pivoted at one end 46 to base 12 for movement about a vertical axis. A coil spring 50 acting between the lever and front wall 18 normally urges the free end 52 of lever 42 towards the housing front wall 18 (FIG. 1). Thus, the movement of bar 30 is transmitted by pin 44 to lever 42 for moving the lever in a horizontal plane about the vertical axis and against the bias of spring 50.

Figure 2:
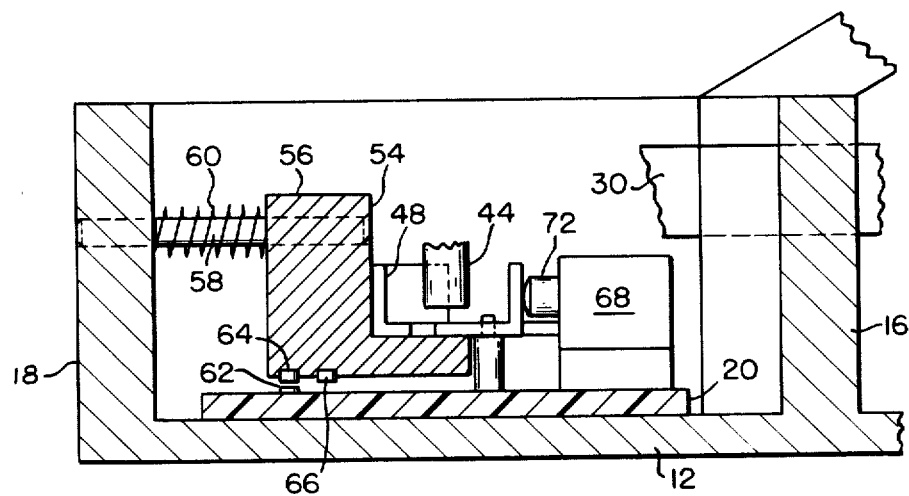
FIG. 2 is a view taken along 2—2 of FIG. 1 on an enlarged scale.

As shown in FIGS. 1 and 2, the free end 52 of the lever rests against an end surface 54 of a movable control element 56. It should be appreciated that there is only one movable control element 56 and that the free end 52 of each of the two levers 42 bear against the control element end surface 54.

The movable control element 56 is slidably mounted on one or more guide rods 58 fixed to and extending inwardly from the rear wall 18 of the housing. A coil spring 60 between the housing wall and the control element 56 urges the control element to the right as viewed in FIG. 2 or toward the housing front wall 16.

Control element 56 can be a movable portion of any suitable signal generator which generates an output in proportion to the relative position of the control element, as for example, the wiper of a potentiometer. It is preferred, however, that the signal generator be a device which operates according to a Hall effect. Such a device is known in the art as including an element which is capable of generating an electrical signal in proportion to a magnetic field. As shown in FIG. 2, such a Hall element 62 is attached to circuit board 20 beneath movable control member 56. Mounted to the movable member and over the Hall element are two permanent magnets 64 and 66. Both magnets are positioned about 0.1 millimeter above the Hall element and are arranged so that one magnet 64 has its north pole towards the Hall element while the other magnet 66 has its south pole towards the Hall element.

When the foot pedals are at a rest position, the north pole of magnet 64 is disposed directly over the Hall element 62 causing a high electrical resistance in the Hall element and a low voltage output.

The second permanent magnet 66 is moved toward the Hall element as either foot pedal is depressed and is located directly over the element at maximum depression of the foot pedal. Since the second permanent magnet 66 has its south pole toward the Hall element, moving this magnet over the Hall element reverses the direction of the magnetic flux. This causes a low electrical resistance in the Hall element so as to increase the voltage output. According to this arrangement, and by appropriate selection of the dimensions between the two permanent magnets and their respective fields of strength a control voltage can be produced which is variable between about 0.5 and 5.0 volts and which is proportional to the relative position of the movable control member 56 over the Hall element 62.

Completing the structure the foot controller shown in FIG. 1 is a pair of switches 68, 70 attached to the circuit board 20 within housing 14. Each switch lies in the control circuit of an appropriate utility such as water or air. Each switch also is associated with one of the levers 42 and each switch has a contact 72 operated by the associated lever. When the appropriate foot pedal 24 or 26 is depressed to move lever 42 toward the rear wall of the housing and away from contact 72, the switch is operated to turn on the appropriate utility. However, the rate of flow of the utility is determined by the output of the Hall element 62 and as set out hereinabove, this is determined by the relative position of the movable control member 56 over the Hall element.

To facilitate operation of the foot pedals, a spring 74, attached to base 12, extends beneath both foot pedals to bias the foot pedals in an upward direction.

Thus, it should be appreciated that the foot controller, as thus far described, can be used to control any one of a number of dental instrument such as a syringe, air or electrically powered drill, ultrasonic scaler or the like. In this respect, it is very common in the practice of dentistry to have all of the above instruments housed in a single dental unit. It is also common to have mechanical, electrical or pneumatic trigger circuits associated with each of these instruments, such that when the instrument is lifted from its holder, the instrument is automatically coupled to the appropriate utility supply for powering that instrument. For example, if the selected instrument is an air-powered drill, means are known in the art which will automatically couple the foot controller to the high pressure air supply powering the drill. Thereafter, the dentist simply has to step on pedal 24. This moves bar 30 toward the housing rear wall 18 in an amount sufficient to carry the upstanding portion 48 of lever 42 away from switch contact 72. Opening the contact thus arms or readies an air control valve (not shown). Thereafter, continuing to depress foot pedal 24 will vary the voltage output of Hall element 62 as described hereinabove to control the opening of the air flow valve so that the amount of air flow is determined by the voltage output of the Hall element. In this way, the dentist can control the speed of the air driven handpiece.

As another example, if the dentist lifts a syringe from its holder, means are known to couple the foot controller to the air and water supplies for the syringe. With the controller as described, the dentist stepping on one pedal can initiate and control the flow of air from the syringe whereas stepping on the other pedal can initiate and control the flow of water to the syringe. Stepping on both pedals simultaneously, initiates both air and water flow to produce a controlled spray.

With the operation of only one of the foot pedals, the movable control member 56 separates from the lever 42 associated with the pedal not operated. The lever not operated is maintained in the rest position by the action of the associated spring 50 and the foot pedal not depressed is maintained in its rest position by the action of a corresponding spring 40 acting on bar 30.

Thus, it should be appreciated that the present invention provides a foot controller capable of controlling the operation of a plurality of different dental instruments using a relatively simple foot pedal mechanism and connecting linkages to operate both switches and a variable signal generator.

We claim:

1. A foot controller for initiating and controlling the flow of a utility service to a dental instrument, said controller comprising:
(a) a housing adapted to rest on a floor surface, said housing having front and rear walls;
(b) a pair of foot pedals hinged to said housing for movement about a horizontal axis;
(c) bias means for urging said pedals upwardly to a rest position;
(d) a signal generator within said housing including a single movable control element, said generator producing an output signal in response to the movement of said control element;
(e) means operatively connecting each of said pedals with said single control element for moving said element responsive to either independent or simultaneous movement of said foot pedals; and
(f) an on-off switch associated with each foot pedal for switching on a utility supply responsive to movement of said foot pedals against said bias means.

2. A foot controller as in claim 1 including a guide bar horizontally mounted in said housing, said single control element being slidably mounted to said guide bar and a spring on said guide for urging said control element to one end of said guide bar.

3. A foot controller as in claim 2 wherein:
(a) said signal generator includes a Hall element; and
(b) a pair of spaced permanent magnets carried by said single movable control element, said magnets being arranged to maximize the electrical resistance of said Hall element when said control element is at said one end of said guide bar and to reduce the electrical resistance of said Hall element when said control element is moved on said guide bar against said spring.

4. A foot controller as in claim 1 wherein said means operatively connecting each foot pedal with said single movable control element comprises:
(a) a pair of independently movable lever arms in said housing, each being pivoted at one end and each having a free end disposed adjacent said movable control element; and
(b) drive means between said foot pedals and lever arms for driving a selected one of said lever arms about its pivot responsive to depressing a selected one of said foot pedals thereby moving the free end of said selected lever arm against said control element to move the same.

5. A foot controller as in claim 4 wherein said drive means comprises:
(a) an axially movable bar carried by said housing, said bar having an end face engagable by one of said foot pedals;
(b) a first spring for urging said bar towards said one foot pedal wherein stepping on said pedal moves said bar against the bias of said first spring; and
(c) a pin on said bar for engaging and moving one of said lever arms responsive to axial movement of said bar against the bias of said first spring.

6. A foot controller as in claim 5 including:
(a) a second spring normally urging each of said lever arm in a direction away from said single, movable control element; and
(b) a third spring normally urging said movable control element in a direction towards said lever arms.

7. A foot controller as in claim 4 wherein each of said on-off switches has a contact in engagement with one of said lever arms whereby movement of said lever arm towards said control element operates said switch.

8. In a foot controller including a housing adapted to rest on a floor surface, a pair of foot pedals pivoted to the housing for movement about a horizontal axis, a spring for urging each foot pedal upwardly to a rest position, on-off switches associated with each foot pedal, and a signal generator within the housing capable of producing an output voltage in direct proportion to the movement of either foot pedal from its rest position, the improvement comprising:
(a) a single control element associated with both said foot pedals and said signal generator, said control element being mounted in said housing for rectilinear movement to
   a first position wherein the output from said signal generator is a minimum and
   a second position wherein the output from said signal generator is a maximum;
(b) a spring urging said control element to said first position; and
(c) drive means between each of said foot pedals and said single control element for moving said element against said spring responsive to the either the independent or simultaneous arcuate movement of said foot pedals about said horizontal axis.

9. A foot controller as in claim 8 wherein said drive means comprises:
(a) first means for transforming the arcuate movement of said foot pedals to rectilinear motion;
(b) second means for transforming the rectilinear movement of said first means to arcuate movement; and
(c) third means for moving said control element in a straight line responsive to the arcuate movement of said second means.

10. A foot controller as in claim 8 wherein said drive means comprises:
(a) a bar slidably carried by said housing, said bar having one end face engagable with one of said foot pedals so that arcuate movement of said one foot pedal from its rest position drives said bar axially;
(b) a lever associated with each foot pedal, each lever being pivoted at one end within said housing for movement about a vertical axis, said lever having a free end and being operatively connected to said bar so that axial movement of said bar drives said free end through an arc;
(c) said free end of each lever being adjacent said single control element so that arcuate movement of the free end of either lever will drive said element from said first position and towards said second position; and
(d) spring means operating to bias each lever in a direction away from the second position of said control element.

* * * * *